(12) United States Patent
Leinsing et al.

(10) Patent No.: US 8,740,850 B2
(45) Date of Patent: Jun. 3, 2014

(54) SAFETY CATHETER SYSTEM AND METHOD

(75) Inventors: Karl R. Leinsing, Hampton, NH (US); Matthew R. Shute, Raleigh, NC (US)

(73) Assignee: CareFusion 303, Inc., San Diego, CA (US)

( * ) Notice: Subject to any disclaimer, the term of this patent is extended or adjusted under 35 U.S.C. 154(b) by 123 days.

(21) Appl. No.: 13/225,229

(22) Filed: Sep. 2, 2011

(65) Prior Publication Data

US 2011/0319827 A1 Dec. 29, 2011

Related U.S. Application Data

(63) Continuation of application No. 11/585,434, filed on Oct. 23, 2006, now Pat. No. 8,029,472, which is a continuation of application No. 10/334,125, filed on Dec. 30, 2002, now Pat. No. 7,125,396.

(51) Int. Cl.
*A61M 5/178* (2006.01)
(52) U.S. Cl.
USPC .................................. 604/165.01; 604/164.01
(58) Field of Classification Search
USPC ...................................................... 604/167.03
See application file for complete search history.

(56) References Cited

U.S. PATENT DOCUMENTS

| | | | | |
|---|---|---|---|---|
| 4,917,669 A | * | 4/1990 | Bonaldo | 604/192 |
| 5,562,631 A | * | 10/1996 | Bogert | 604/192 |
| 5,672,160 A | * | 9/1997 | Osterlind et al. | 604/263 |
| 5,725,503 A | * | 3/1998 | Arnett | 604/162 |
| 6,213,978 B1 | * | 4/2001 | Voyten | 604/164.01 |

* cited by examiner

*Primary Examiner* — Jason Flick
*Assistant Examiner* — Weng Lee
(74) *Attorney, Agent, or Firm* — McDermott Will & Emery LLP

(57) ABSTRACT

A catheter integral with a valved needle-free connector provides a safety catheter device configured to receive a blunt cannula and sharp needle forming an insertion mechanism. The sharp needle is mounted within a needle tube and a control handle is used to slide the sharp needle out of and into the protective needle tube. When the insertion mechanism is mounted to the connector and the control handle is used to slide the sharp needle out of the tube, a blunt cannula first moves into contact with and enters the bore of the valve mechanism of the connector opening it and protecting it from damage that may be caused by the sharp needle. The sharp needle is then extended through the connector and extends out the distal end of the catheter so that a venipuncture procedure may be performed to properly locate the catheter in the patient's circulatory system. Once located, the needle may be retracted into the insertion mechanism, the insertion mechanism disconnected from the connector, and discarded.

11 Claims, 12 Drawing Sheets

SAFETY CATHETER SYSTEM AND METHOD

This application is a continuation of U.S. application Ser. No. 11/585,434, filed on Oct. 23, 2006, now pending, which is a continuation of U.S. application Ser. No. 10/334,125, filed Dec. 30, 2002, now U.S. Pat. No. 7,125,396, all of which are incorporated herein by reference.

BACKGROUND

The present invention relates generally to intravenous catheters, and more particularly to an intravenous catheter having a connector operable with a blunt cannula to control the flow of fluid through the IV catheter.

Intravenous (IV) therapy is a versatile technique used for the administration of medical fluids to patients. It has been used for various purposes such as the maintenance of fluid and electrolyte balance, the transfusion of blood, the administration of nutritional supplements, chemotherapy, and the administration of drugs and medications. Fluids may be administered intravenously by injection through a hypodermic syringe, or intermittently or continuously by infusion using a needle or a plastic or silicone catheter.

Although there are many advantages to be derived by the patient from the intravenous administration of fluids, the past two decades have brought heightened awareness of the risks of propagating infectious diseases associated with the technique, particularly due to the HIV virus. One method by which infectious disease may be spread is an inadvertent puncture of medical personnel by the sharp needle that was used to insert an IV catheter into an infected patient. Such needles are extremely sharp and should the insertion site become wet with administration fluid or blood, the medical personnel may inadvertently puncture herself or himself while handling the sharp needle. Any opening in the skin raises the possibility of contracting an infection.

One consequence of this heightened awareness has been the development of various devices designed to reduce the risk of spreading infectious diseases during the IV procedure. Devices have been developed over the years to attempt to lower the risk of such inadvertent punctures. One such class of devices has been the blunt cannula approach to connectors. In this class of connectors, sharp needles are not used. In one approach in this class, the connecting devices have been designed based on the Luer system of connectors in which the mating surfaces are tapered. While this approach has advanced the safety of health care workers substantially, a venipuncture procedure still requires the use of a sharp needle.

Another class of devices developed in the venipuncture area is the safety needle. This is a type of needle housed inside a protective guard. It comprises a sharp needle that may be extended from and retracted into the protective guard, the purpose of which is to lessen the chance of an inadvertent needle puncture of medical personnel. It provides the required sharp needle for the venipuncture procedure but carefully guards the operator against the sharp needle except for the one time it is extended to pierce the patient. In some versions, the sharp needle is locked within the protective guard once it has been retracted. The possibility of an inadvertent puncture is further reduced with such an arrangement.

Catheters used for peripheral IV therapy tend to be relatively short, between 19 mm and 32 mm long, although they are occasionally 50.8 mm long for insertion into a deep vein. A peripheral IV catheter is made of soft, flexible plastic or silicone, generally between 16 gauge and 24 gauge. In the conventional venipuncture procedure, the catheter is inserted into a vein in the patient's hand, foot, or the inner aspect of the arm or any vein in the body that will accept an IV catheter.

IV catheters are used to provide fluid to or to withdraw fluid from a patient. In order to properly place an IV catheter in a patient's vein, a sharp introducer needle must be used to puncture the skin, tissue, and vein wall to provide a path for placement of the catheter in the vein. Typical IV catheters are "over-the needle" catheters where the catheter is coaxially placed over the needle. The catheter thus rides with the needle through the skin, tissue, and vein wall and into the patient's vein. When the needle pierces the vein, blood will "flashback" into the needle. Thus, once the clinician observes this flashback of blood, the clinician will know that the catheter and needle have been inserted in the vein. The needle can then be withdrawn from the patient and the catheter can be advanced further into the vein as desired.

In further detail, a tourniquet is applied proximal to the venipuncture site and a variety of techniques may be used to dilate the vein. While wearing disposable gloves, the medical technician cleanses the venipuncture site and a vein is retracted or anchored by placing a thumb over the vein about 50 mm to 75 mm distal to the site. A catheter with a sharp stylet or needle advanced through its lumen so that the sharp tip extends beyond the cannula of the catheter, or a butterfly needle, is introduced into the vein by inserting the bevel into the vein at about a 20 degree to 30 degree angle with the bevel facing up in order to pierce one wall of the vein. Blood return in the tubing of the butterfly needle or a flashback chamber of the over-the-needle catheter indicates that the vein has been entered, and the needle is lowered towards the skin to decrease the entry angle and the catheter is advanced about 6.35 mm into the vein. The sharp needle or stylet is loosened and the catheter is gently advanced farther up into the vein until the hub of the catheter is against the venipuncture site. The tourniquet is loosened and the sharp needle or stylet is removed from the catheter. The needle adaptor of the infusion tubing is secured to the hub of the catheter, and the roller clamp is opened. The flow rate may be controlled either by adjusting the amount of pressure exerted by the roller clamp or by adjusting the infusion rate of an infusion pump. The catheter is secured to the venipuncture site by gauze and adhesive tape.

During the above venipuncture procedure, medical personnel are exposed to the possibility of an accidental needle puncture or to contamination from the back flow of the patient's blood from the venipuncture site. While care is usually taken to avoid a puncture of the medical personnel, circumstances may arise during which a puncture of the medical personnel may nevertheless occur exposing the health care personnel to any infectious blood borne diseases carried by the patient.

Devices have been developed to reduce the risk of such accidental needle punctures, but a need has been recognized for devices that efficiently prevent the back flow of blood while providing a swabbable female Luer port. In one case, there has been provided an intravenous catheter insertion apparatus that includes a catheter integral with a connector having a pre-slit septum. A blunt cannula is used to penetrate the pre-slit septum and a needle tube having a sharp needle of sufficient length to pass through the blunt cannula, the connector, and the catheter is attached leaving the sharp tip of the needle projecting beyond the end of the catheter. After the catheter has been inserted into the blood vessel of the patient, the needle tube and blunt cannula may be removed from the connector/catheter device and during removal, the septum of the injection site prevents blood from leaking out of the catheter. Also during removal, the sharp needle tip may be withdrawn into the needle tube that provides a guard over the sharp needle tip to protect the medical personnel performing the IV procedure from puncture.

However, a problem that may result from such an assembly using a pre-slit septum in the connector/catheter device is the possibility of damage to the septum due to the blunt cannula being repeatedly forced into the normally closed pre-slit septum. A damaged septum may leak blood and this may then expose a health care provider to any infectious diseases contained in the blood. A further problem that may arise during the use of such an assembly is that some guarded needle devices available today are somewhat complex with multiple stops and locking devices designed to protect the medical personnel from needle punctures. Unfortunately, the action of sliding the needle into the fluid path created by the blunt cannula and the pre-slit septum with these complex devices may require more than one physical hand movement by the medical personnel operating the assembly. Because medical personnel are quite busy, any additional efforts required to accomplish tasks are undesirable. Further, the requirement of extremely fine motor skills during the placement of a sharp needle in a catheter and into a patient can result in inadvertent damage to the connector of the catheter resulting in blood leakage.

Pre-slit septum systems also do not typically allow access to the catheter with standard male Luer connectors. An adapter is required, which is not desirable. In addition to the expense of an additional part, such adapters can get lost or may not be in stock when needed.

Hence, those skilled in the art have recognized a need for a safety catheter insertion device that provides increased protection from needle punctures to medical personnel handling the device. Additionally, a need has been recognized for a more reliable insertion device that is less likely to leak a patient's blood after removal of the catheter needle and even after continued reuse of the device. A further need has been recognized for an insertion device that is easier to use so that less effort, steps, and time are required to accomplish the placement in the patient. And furthermore, an insertion device that is easier to manufacture and that is cost effective is also needed. The present invention satisfies these needs and others.

SUMMARY OF THE INVENTION

Briefly, and in general terms, the invention is directed to a safety catheter system and method that provides access to a biological site. In one aspect, the safety catheter system comprises a catheter defining a lumen and having a first end for insertion into the biological site and a second end connected to a valved connector for controlling the flow of fluid through the lumen of the catheter. The connector has an internal fluid passageway by which fluid may flow through the connector with the connector comprising a housing having a first port and a second port, the first port being adapted to receive a blunt cannula, such as a male Luer fitting, and the second port being connected to the second end of the catheter. A movable element is positioned within the housing, the movable element having a first position at which the movable element blocks fluid flow through the housing and a second position at which the movable element permits fluid flow through the housing. In a more detailed aspect, the movable element comprises a head defining a bore forming a part of the fluid passageway through the connector, the head being configured such that when the movable element is in the second position, the bore assumes it naturally open configuration thereby permitting fluid flow through the connector and cannula, the head being further configured such that when the moveable element is in the first position, the bore moves to a closed configuration preventing fluid flow.

In more detailed aspects, the safety catheter further comprises an insertion mechanism that comprises a blunt cannula adapted for insertion through the first port of the housing and into contact with the head of the movable element to move the movable element to the second position at which position the bore opens. The blunt cannula is also adapted to slide within the opened bore of the head of the movable element to protect the movable element, and a needle having a sharp tip is slidably engaged with the blunt cannula and is adapted to extend through the blunt cannula after the blunt cannula has slid within the bore of the movable element, and to slide through the catheter until the sharp tip projects beyond the first end of the catheter so that the sharp tip may penetrate the biological site. The insertion mechanism comprises a needle tube in which is located the blunt cannula and the sharp needle. The needle tube comprises threads located adjacent the first port that threadably engage the needle tube.

In yet other aspects, the needle tube of the safety catheter system and method further comprises a control handle that controls the position of the blunt cannula and the sharp needle. The control handle is configured such that when it is in a retracted position, the sharp tip of the needle is covered by the needle tube to protect a clinician from being punctured by the sharp tip. When the control handle is in the extended position, the blunt cannula first protrudes from the needle tube to engage the movable element of the connector as described above, and the sharp needle is then extended from the needle tube to extend through the connector and the cannula so that the biological site may be accessed. Further, the needle tube comprises a limiting device adapted to limit the sliding travel of the blunt cannula, and is further adapted to provide a restraint against the sharp needle tip projecting beyond the end of the blunt cannula before the blunt cannula reaches the limit of travel.

In another aspect, the needle tube comprises a locking device to retain the needle in a retracted position within the needle tube once the sharp needle has been retracted. The locking device permanently retains the sharp tip of the needle within the tube to protect clinicians against being punctured by the needle. In another aspect, the movable element includes a head having a bore through which fluid flows through the connector. The bore is marquise-shaped and is naturally open. The connector includes a larger inner diameter section at the second position of the movable element such that the bore may resume its naturally open configuration and permit fluid flow through the connector and the catheter.

In accordance with method aspects of the invention, there is provided a method for providing access to a biological site through placement of a catheter in the site. The method comprises moving a blunt cannula into a first port of a connector into contact with a movable element of the connector to move the movable element into a housing of the connector to a position where the movable element opens to permit flow of fluid through the connector, the blunt cannula also moving into the opening of the movable element to provide protection to the movable element, sliding a needle having a sharp tip through the blunt cannula and through a catheter connected to the connector so that the sharp tip of the needle extends beyond the catheter a sufficient length that enables an operator to access a biological site with the sharp needle and catheter. retracting the sharp needle from the catheter and the blunt cannula, removing the blunt cannula from the connector, and moving the movable element of the connector to a closed position at which the movable element prevents flow of fluid through the catheter.

In accordance with more detailed aspects, the method further comprises the step of protecting the sharp tip of the needle with a physical barrier whereby the possibilities of a operator being punctured with the sharp tip are reduced. Further, the of moving a blunt cannula into a first port of a connector into contact with a movable element comprises moving the movable element into a second position within a housing of the connector at which position a bore through the movable element resumes its naturally open shape providing a fluid flow passageway through the connector, and moving the blunt cannula into the bore of the movable element to provide protection to the movable element. Additionally, the method further comprises the steps of limiting the movement of the blunt cannula to a position within the connector to entering the open bore, and restraining the sharp needle tip from projecting beyond an end of the blunt cannula before the blunt cannula reaches the limit of its movement.

In yet further detailed aspects, the method further comprises the steps of threadably connecting an insertion mechanism to the connector, the insertion mechanism containing the blunt cannula and the sharp needle, and unthreading the insertion device from the connector after the biological site has been accessed whereby the insertion device containing the sharp needle may be discarded. Additionally, the method further comprises the steps of controlling the position of the sharp needle in the insertion mechanism with a control handle, wherein moving the control handle to a retracted position causes the sharp needle to be moved to a retracted position within the insertion mechanism so that the insertion mechanism covers the sharp tip of the needle, and moving the control handle to an extended position causes the sharp needle to be extended from the insertion mechanism so that the sharp needle may be extended through the catheter and used to access the biological site. In yet a further step, the method comprises locking the sharp needle in a retracted position within the insertion mechanism after its use in accessing the biological site at which position the sharp tip of the needle is protected.

Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

Figure 1:
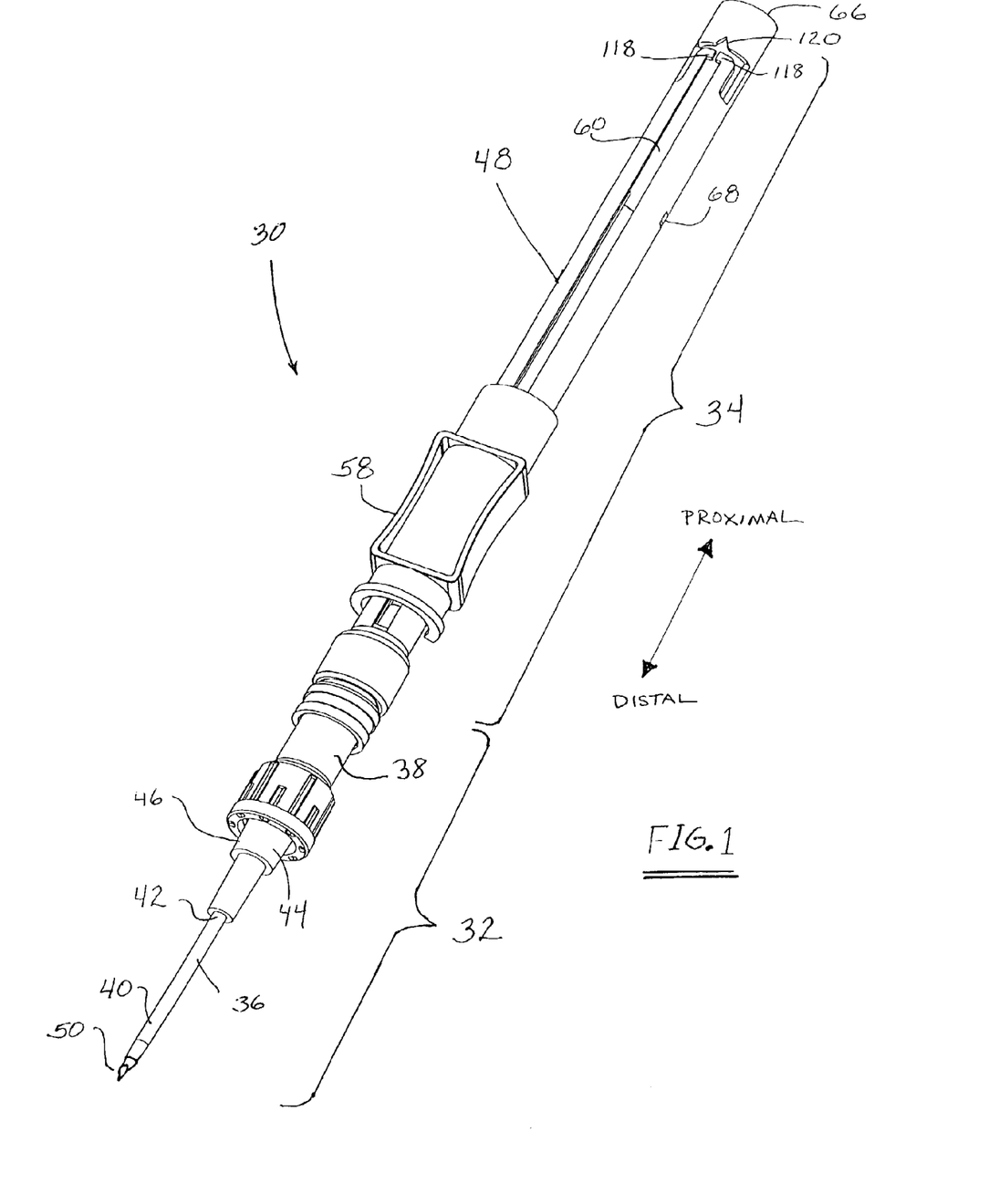
FIG. 1 is a perspective view of an intravenous safety catheter system in accordance with aspects of the invention, the system having a safety catheter device with a sharp needle insertion mechanism mounted to the safety catheter device, and as shown, the insertion device has been activated to extend the sharp tip of the needle from the proximal end of the catheter in preparation for a venipuncture procedure.
Figures 2, 3:
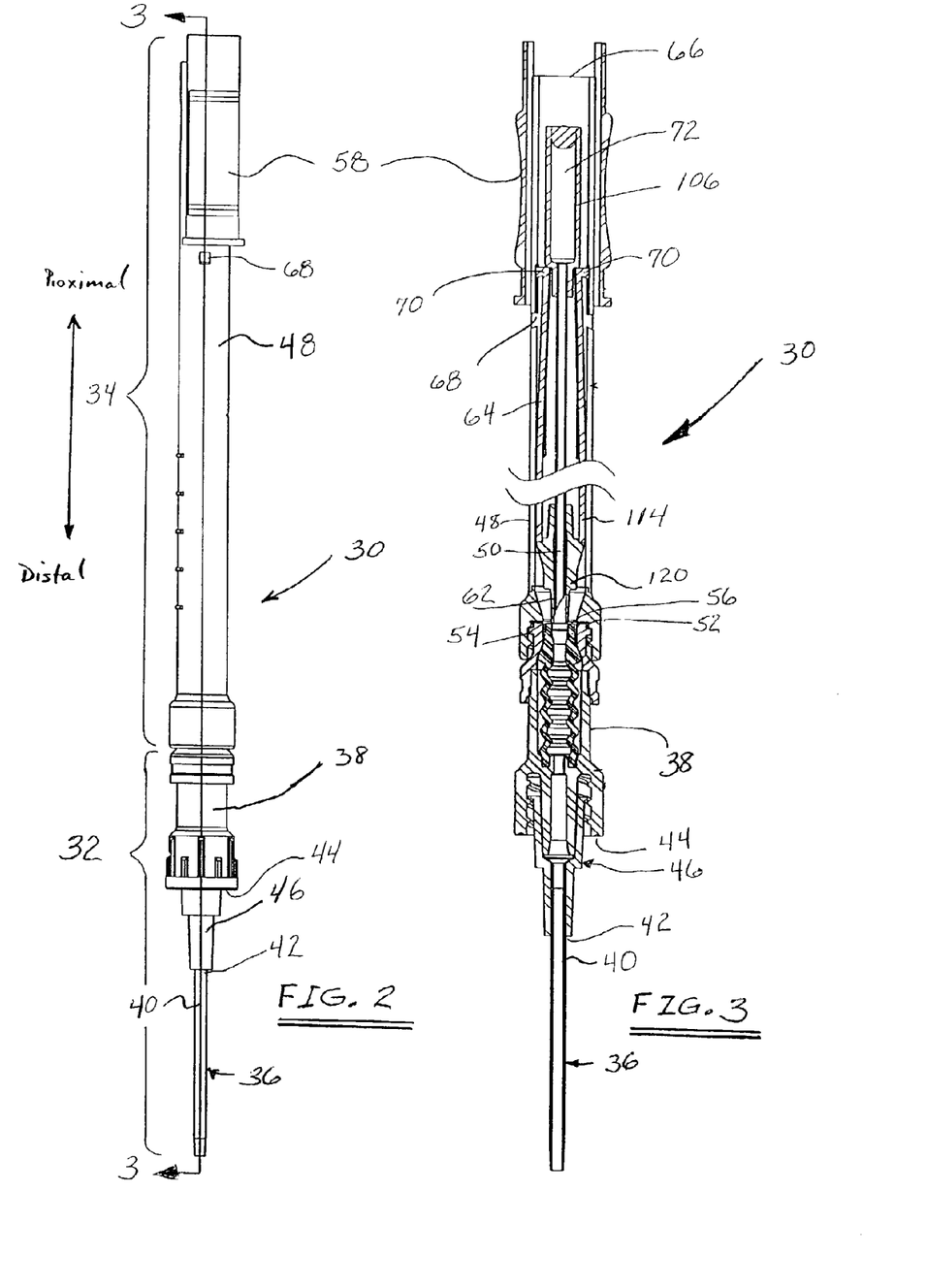
FIG. 2 is a side, elevation view of the safety catheter system of FIG. 1 that has been rotated approximately ninety degrees and shows the insertion mechanism in the pre-use configuration with a control handle of the insertion mechanism located at the proximal, pre-use position where a blunt cannula and the sharp needle are both retracted in the needle tube.
FIG. 3 is a cross sectional view of the safety catheter system of FIG. 2 rotated ninety degrees from the view of FIG. 2 and showing internal details of the insertion mechanism connected to a valved connector which is in turn connected to a catheter for accessing a biological site.

Referring now to the drawings in which like reference numerals indicate like or similar elements among the several views, FIGS. 1, 2, and 3 show different views of an intravenous safety catheter insertion device 30 comprising a safety catheter device 32 to which is mounted an insertion mechanism 34. The safety catheter device 32 comprises a catheter 36 and a valved connector 38 mounted to the catheter. The catheter 36 is of a conventional type well known in the art, and comprises a soft flexible body or tube 40 made from plastic or silicone mounted at its proximal end 42 to the distal end 44 of the connector 38. In this embodiment, the catheter tube 40 is connected to the connector 38 with a female Luer adapter 46. The catheter tube 40 is generally between 19 mm (0.75 inches) and 31.75 mm (1.25 inches) in length and between 16 and 24 gauge in diameter, although other sizes may be used. The insertion mechanism 34 comprises a needle tube 48 within which is housed a sharp needle 50 (FIG. 3). The needle is slidable in the needle tube 48. It should be noted that FIG. 1 shows the sharp needle 50 in an extended configuration with the sharp tip apparent beyond the end of the catheter tube 40 in preparation for performing a venipuncture procedure. FIGS. 2 and 3 however show the sharp needle 50 in a retracted position with the needle fully protected by the needle tube 48.

The connector 38 shown in this embodiment is the ALARIS Medical

Systems, Inc. SmartSite® connector having an internal valve. See for example U.S. Pat. No. 5,676,346 to Leinsing, entitled "Needleless Connector Valve" issued Oct. 14, 1997, incorporated herein by reference. At the proximal end of the connector 52, there are threads 54 and a female Luer adapter port 56 to which the sharp needle insertion mechanism 34 is mounted. At the distal end of the connector 44 the catheter is permanently mounted, as will be discussed in further detail below.

Regarding the view of the insertion mechanism 34 in FIG. 1, a control handle 58 is shown that slides on the tube 48 of the insertion device to control the relative positions of internal components relative to the connector 38. An access slot 60 can be seen in the wall of the needle tube 48 through which the control handle connects with internal components to move them in accordance with movement of the control handle. In the configuration of FIG. 1, the control handle 58 is in its distal position which has caused the sharp needle 50 to extend through the connector 38, through the catheter 36, and to extend from the distal end of the catheter for use in penetrating the patient's skin and blood vessel to place the catheter in the bloodstream. The insertion mechanism 34 also includes a blunt cannula 62 coupled to a cannula control tube 64, both of which are shown in a retracted position in FIG. 3. The blunt cannula 62 surrounds the sharp needle 50 and its use will be explained in further detail below. Near the proximal end 66 of the insertion mechanism, locking slots 68 can be seen that will permanently lock tabs 70 of the cannula control tube 64 into the wall of the needle tube 48 when the cannula control tube 64, and the blunt cannula 62, have been fully extended, as will be shown in more detail in FIG. 9. Also shown in FIG. 3 is a flashback chamber 72 located at the proximal end of the sharp, hollow needle 50. The flashback chamber 72, needle tube 48, cannula control tube 64, and control handle 58 are formed of a clear material so that the contents of the flashback chamber 72 can be seen by an operator of the safety catheter insertion device 30.

As shown in FIG. 3, the sharp needle 50 is in a retracted position within the needle tube 48, and the control handle 58 is also in a retracted position at the proximal end 66 of the needle tube. The tabs 70 of the control tube 64 are located proximal to the locking slots 68 and therefore, the control tube 64 has not yet been used to extend the sharp needle 50 from the needle tube 48. This is a typical configuration for an insertion mechanism 34 that is connected to the connector 38 but has not yet been used to extend the sharp needle 50 through the connector to perform a venipuncture procedure on a patient.

Figure 4:
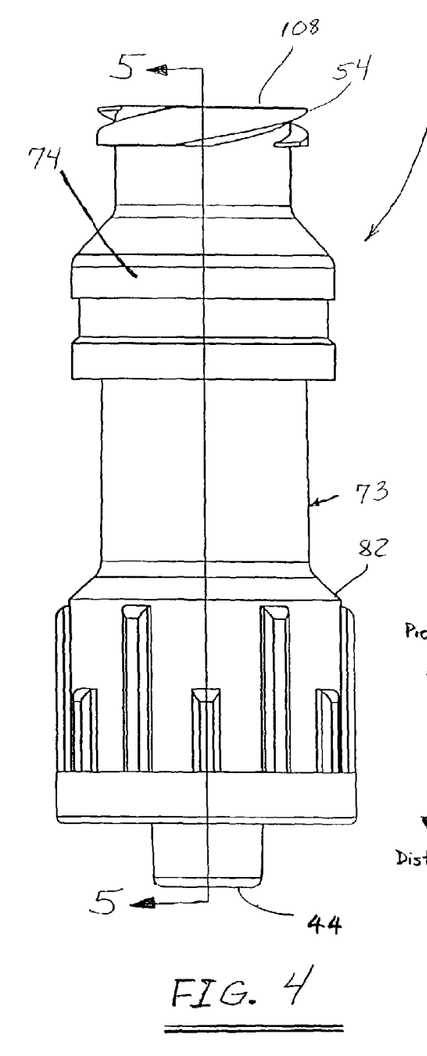
FIGS. 4 and 5 are respectively a side, elevation view and a side cross-sectional view of a valved connector that may be used to form a part of the safety catheter system shown in FIGS. 1 through 3, the connector shown having a female Luer port, a movable element in the form of a piston, and a male Luer port at its distal end.
Figure 5:
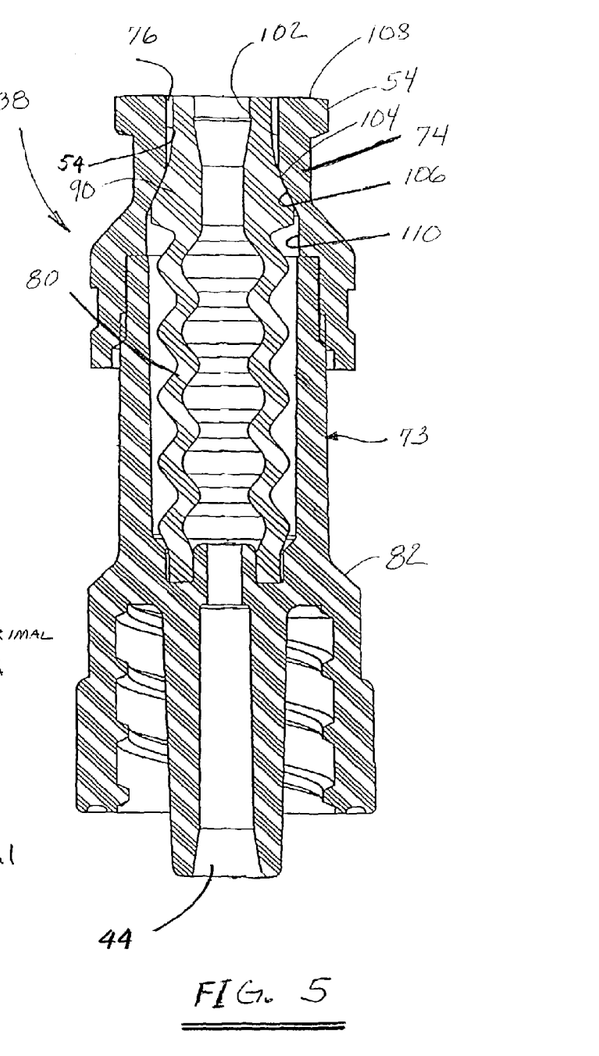

The connector 38 is now shown in greater detail in FIGS. 4 and 5. The connector 38 comprises a housing 73 terminating in an exit port 44 at its distal end, to which the catheter may be attached as shown in FIG. 3. At the proximal end of the housing is located a female Luer adapter 74 for engagement with a male Luer tip or, in this case, the sharp needle insertion mechanism 34, as shown in FIG. 3. The adapter 74 includes a female Luer port 76 and related externally mounted threads 54. The female Luer connection port 76 is configured to receive all ISO standard male luer fittings, as well as other blunt cannulas or fluid conduit devices.

Located within the housing 73 of the connector 38 is a piston element 80. The piston element is resiliently deformable and is captured within the housing 73 between the female Luer adapter 74 and a the base 82 of the housing 73. The piston element's structure, exemplified in detail in FIGS. 5, 6, and 7, generally includes a piston head section 84 and a compressible, or spring, section 86 (see FIG. 6). The piston head section 84 includes a piston head 88 that is elliptical in cross-section and includes a thick taper-lock portion 90 that is circular in cross-section. A marquise-shaped bore 92 is formed in the piston head 88 and terminates in an orifice 73 at its proximal end 75.

Figures 6, 7:
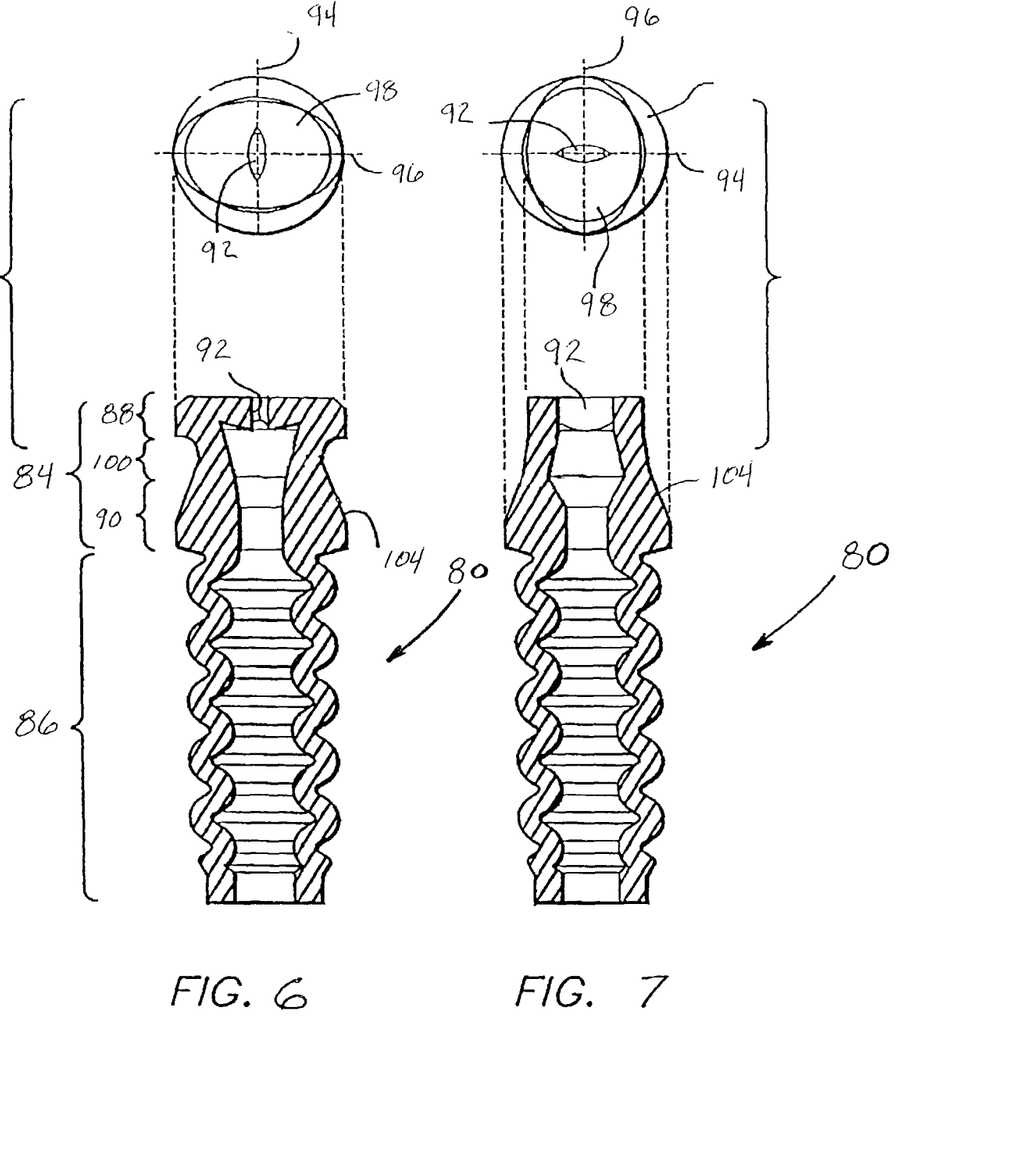
FIGS. 6 and 7 are cross-sectional views of the movable piston element of the valved connector of FIGS. 4 and 5, the views being rotated at ninety degrees to each other.

As is apparent from FIGS. 6 and 7, the marquise-shaped bore 92 is oriented such that its major axis 94 is perpendicular to the major axis 96 of the elliptically-shaped piston head 88. This geometry assists in naturally biasing the marquise-shaped bore 92 into its naturally open position. The naturally open marquise shape of the bore 92 creates an outward force parallel to the major axis 96 of the elliptical shaped piston head 88 and an inward force parallel to the minor axis 94. The inward force tends to compress the piston head 88 in a direction perpendicular to its major axis and thus tends to pull the marquise-shaped bore open when a male luer or other blunt cannula applies force to the top 98 of the piston 80 moving the piston into the center section of the housing 73, as will be shown later. This is accomplished by the elliptical-conical shape of the elliptical conical section 100 that transforms the axial force applied by the male Luer into transverse biasing forces. These biasing forces are what assist the opening of the normally open marquise-shaped bore 92.

The dimensions of the elliptical piston head 88 and the marquise-shaped bore 92 are selected such that when the head is constrained into the circular interior of the ISO Luer taper section 102 of the female luer adapter 74 (see FIG. 5), the bore 92 is completely collapsed and tightly closed off from flow. The tapered shoulder 104 of the taper lock section 90 contacts the ramp/lock section 106 of the female Luer adapter 74 and prevents the top of the piston head 88 from extending beyond the connection port proximal surface 108 to make it substantially flush. The internal diameter of the center section 110 of the Luer adapter 74 is selected such that, when the piston head 88 is positioned therein (shown in FIG. 9), the piston head is free to resume its elliptical shape. This in turn allows the bore 92 to resume its naturally open marquise-shape thereby opening a fluid path through the piston element 80 and the connector 38.

Prior to use the insertion mechanism 34 is initially in its unaccessed state or closed position as shown in FIGS. 2 and 3. The compressible section 66 is pre-loaded and causes the piston head 64 to be biased into the ISO Luer taper section 54 of the female Luer adapter 74 of the connector. The shoulder 104 of the taper-lock section 90 contacts the tapered ramp/lock section 106 of the adapter 74 and prevents the top of the piston head 88 from extending beyond the connection port proximal surface 108 to form a smooth and flush surface. The bore 92 throughout the piston head 88 is tightly squeezed shut by virtue of the normally elliptically shaped piston head being constrained into the circular cross-section of the ISO Luer taper section 54. The sharp pointed ends of the marquise-shaped bore facilitate a tight seal upon compression of the bore along its minor axis 96 by compression of the piston head 68 along its major axis 94. Further details of the operation of the connector may be found in U.S. Pat. No. 5,676,346 to Leinsing, referenced above.

Before connecting the insertion mechanism 34 to the safety catheter device 32, the top or proximal surface 108 of the safety catheter device 32, including the top surface of the piston, may be cleaned. For example, a sterilizing swipe may be passed over the smooth surfaces. The insertion mechanism may then be connected to the safety catheter device as shown in FIGS. 2 and 3. However, in another embodiment, the insertion mechanism may already be connected to the safety catheter device at the factory and no further wiping of the connector will be necessary before its use.

Figure 8:
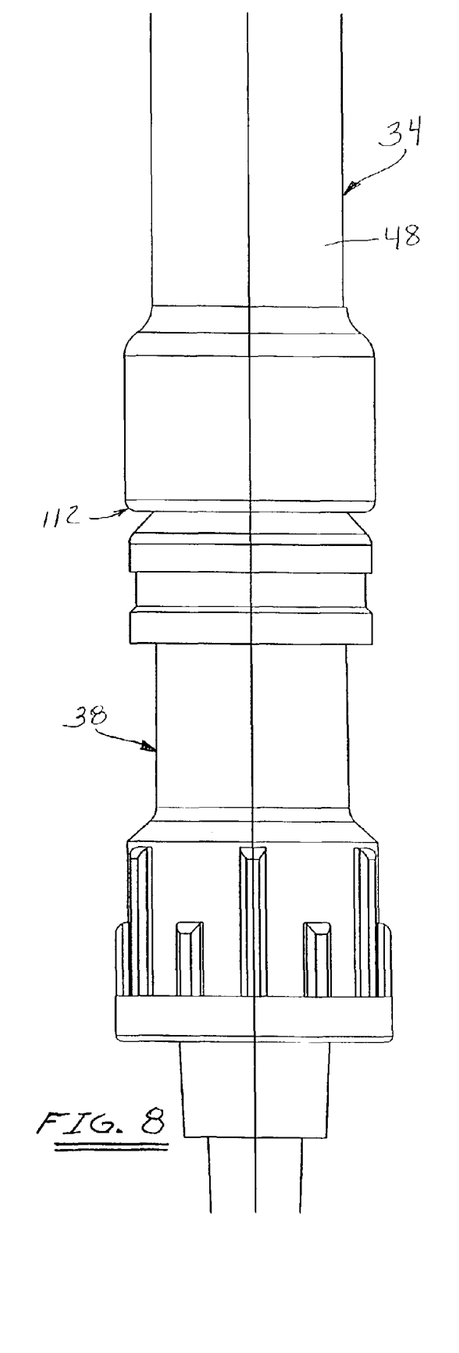
FIG. 8 is a side, elevation view showing the insertion mechanism mounted to the connector of FIG. 4.
Figure 9:
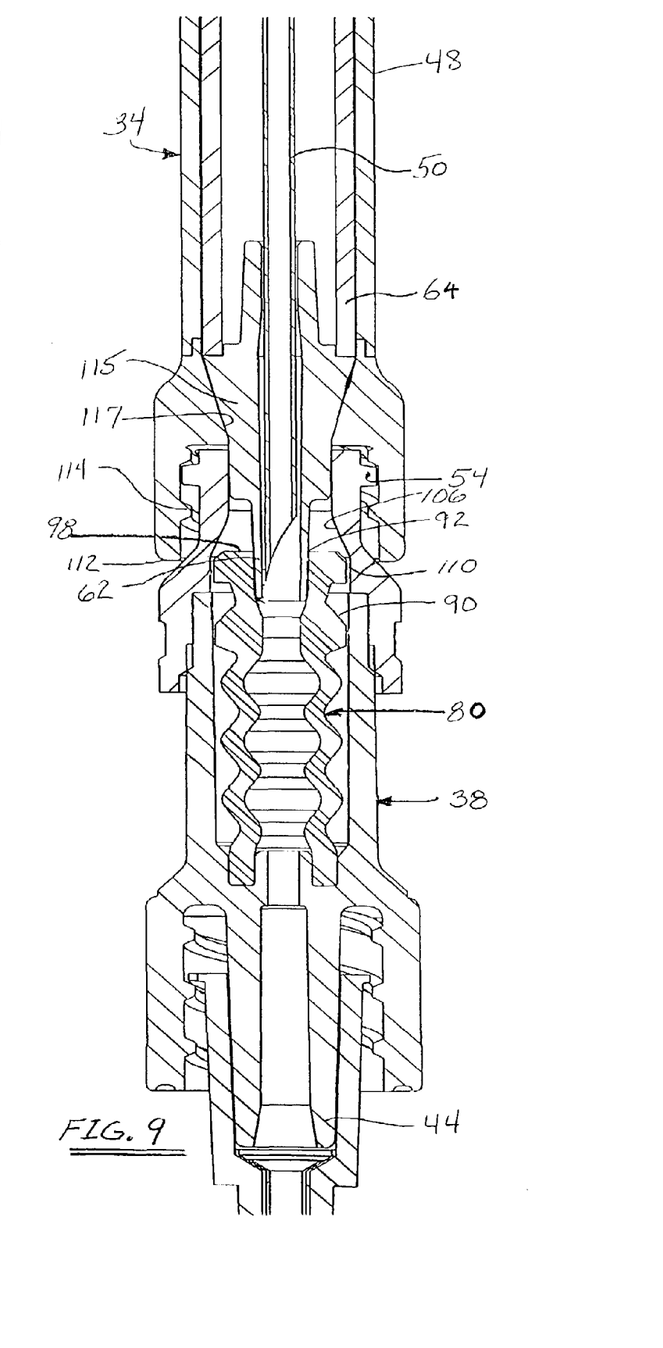
FIG. 9 is a cross-sectional view of FIG. 8 showing the insertion mechanism threadably mounted to the connector with the blunt cannula engaged with the bore of the piston element of the connector, the blunt cannula having entered the open bore of the piston and thereby protecting the bore of the piston element prior to insertion of the sharp needle through the piston element.

The insertion mechanism is connected to the safety catheter device via threaded connection in the embodiment shown and described herein. In particular, as is shown in FIGS. 8 and 9 in greater detail, the distal end 112 of the insertion mechanism 34 includes internal threads 114 that engage the external threads 54 of the connector. The assembly would then appear as shown in FIG. 2. However, other connection approaches may be found to be usable.

Figure 10:
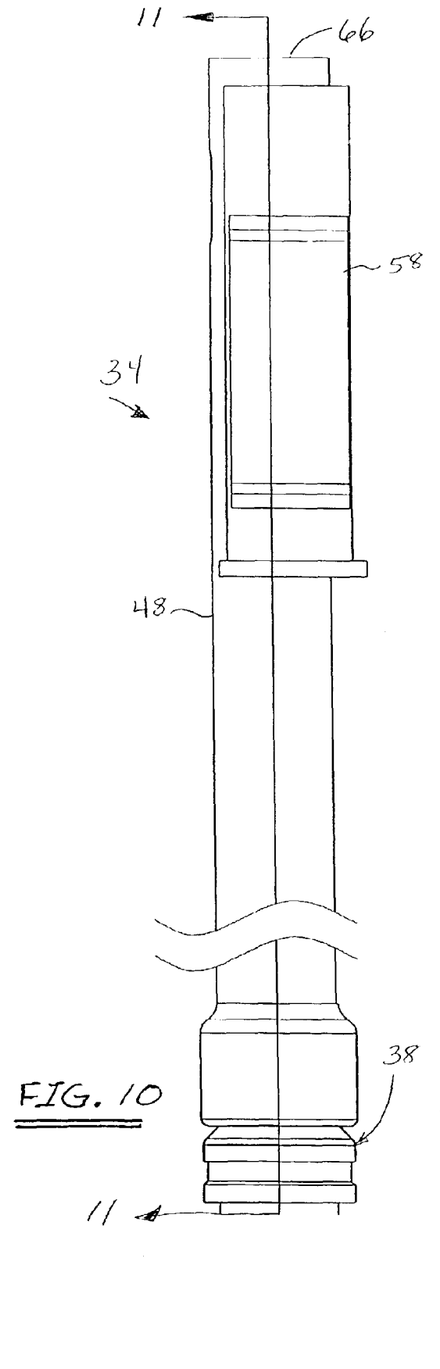
FIG. 10 shows the position of the control handle on the needle tube as the blunt cannula is moved into the position shown in FIG. 9.
Figure 11:
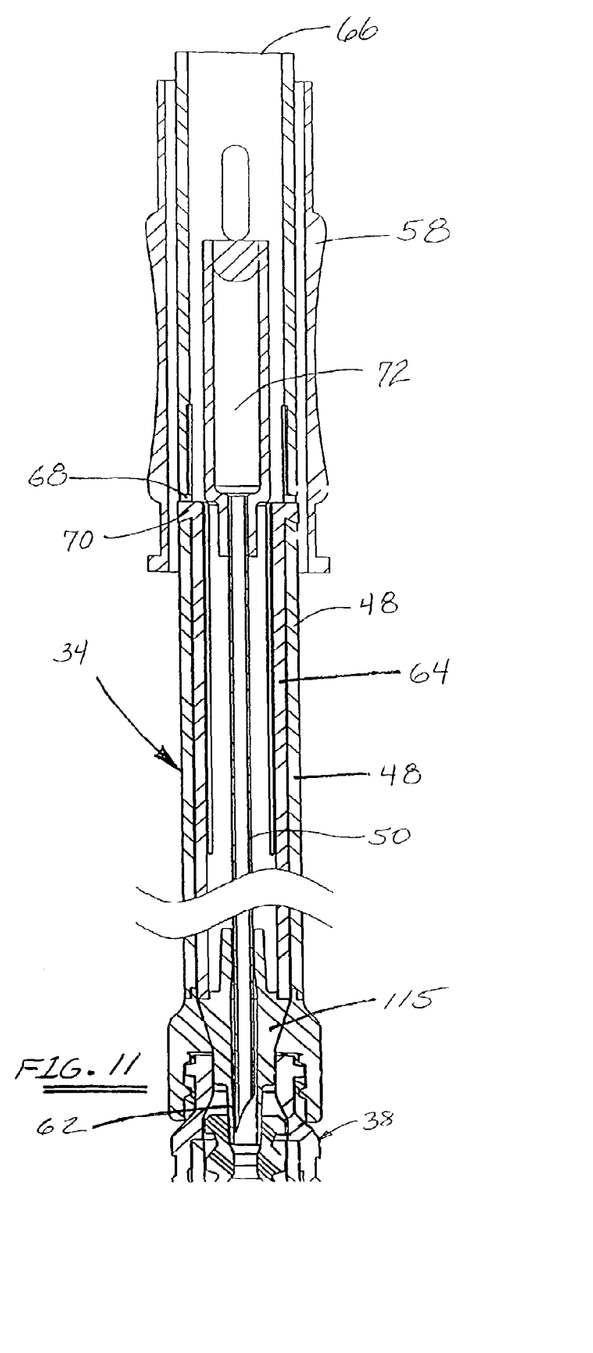
FIG. 11 is a cross sectional view of FIG. 10 showing a blunt cannula control tube locked into position with the blunt cannula therefore locked in position, as shown in FIG. 9.

In FIG. 3, the insertion mechanism 34 is shown in the initial position with the control handle 58 located near the proximal end 66 of the insertion mechanism. The control handle is then grasped by the clinician, such as with a thumb and forefinger, and is slid carefully in the distal direction. As the control handle progresses in the distal direction, the flashback chamber 72 contacts the blunt cannula control tube 64 as shown in FIG. 11 causing it to also move in the distal direction until its locking tabs 70 engage the locking slots 68 in the wall of the needle tube 48. The position of the control handle at this occurrence is shown in FIG. 10. The blunt cannula control tube then no longer interferes with the flashback chamber and the flashback chamber 72/sharp needle 50 can be extended farther. Referring again to FIG. 9, the protecting action of the blunt cannula 62 can be clearly seen. As the control handle is moved distally as shown in FIGS. 10 and 11, the blunt cannula extends from the needle tube 48 into the female port 56 of the female Luer adapter 46 of the connector 38. By pressing the piston head 88 of the piston element 80 into the larger diameter center section 110 of the connector, the naturally open, marquise-shaped bore 92 of the piston is permitted to resume its naturally open shape. At the same time, the blunt cannula 62 is small enough to fit within the bore 92 thereby providing protection to the piston head from possible tearing or puncture that might be inflicted by the sharp needle 50 if it were not housed within the blunt cannula. It will be noted that the sharp needle 50 moves with the blunt cannula 62 into the piston head, as can be seen in FIG. 9. It is at the point of extension into the piston element 80 shown in FIG. 9 that the locking tabs 70 of the blunt cannula control tube 64 protrude into the locking slots 68 of the wall of the needle tube 59 preventing further extension of the blunt cannula into the connector 38.

It may also be noted that the blunt cannula has a tapered base section 115 that tapers outwardly in the proximal direction. The blunt cannula base engages an inwardly tapered section 117 at the distal end 112 of the insertion mechanism 34; i.e., the section tapers inwardly in the distal direction. The two tapers are such that the blunt cannula cannot be removed from the insertion mechanism in the distal direction and the blunt cannula therefore can only extend a predetermined length from the distal end 112 of the insertion mechanism. Thus the blunt cannula control tube 64 need not be rigidly mounted to the blunt cannula 62. When the blunt cannula control tube 64 is locked in position with the locking device of the tabs 70 and the slots 68, the blunt cannula is prevented from moving in the proximal direction by the locking device 70 and from moving in the distal direction by the tapers 115 and 117.

Figure 12:
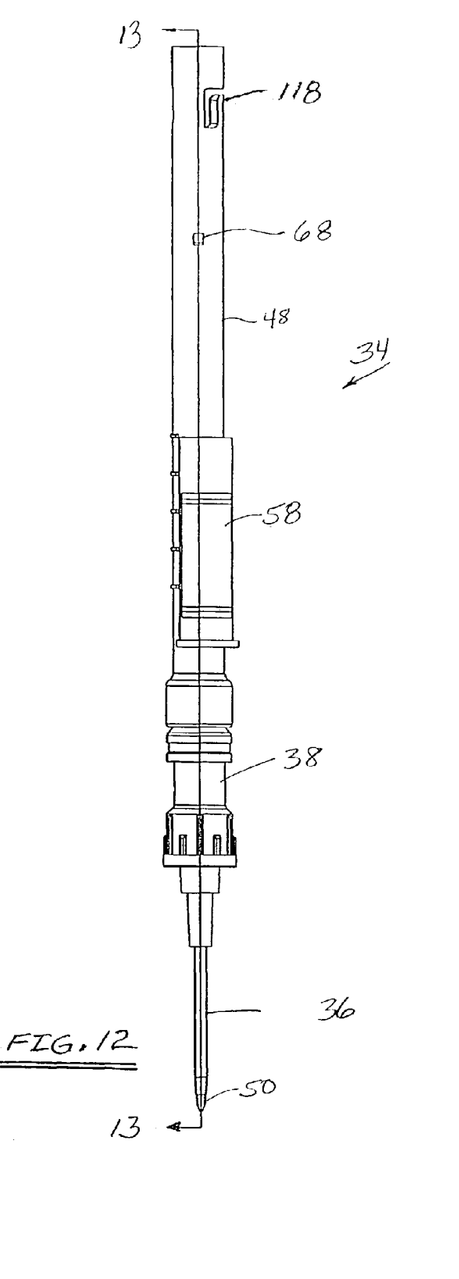
FIG. 12 is a full side, elevation view of the safety catheter system as shown in FIG. 1 in which the insertion mechanism is in the fully activated configuration thereby causing the sharp tip of the needle to protrude from the distal end of the catheter in preparation for performance of a venipuncture procedure.
Figure 13:
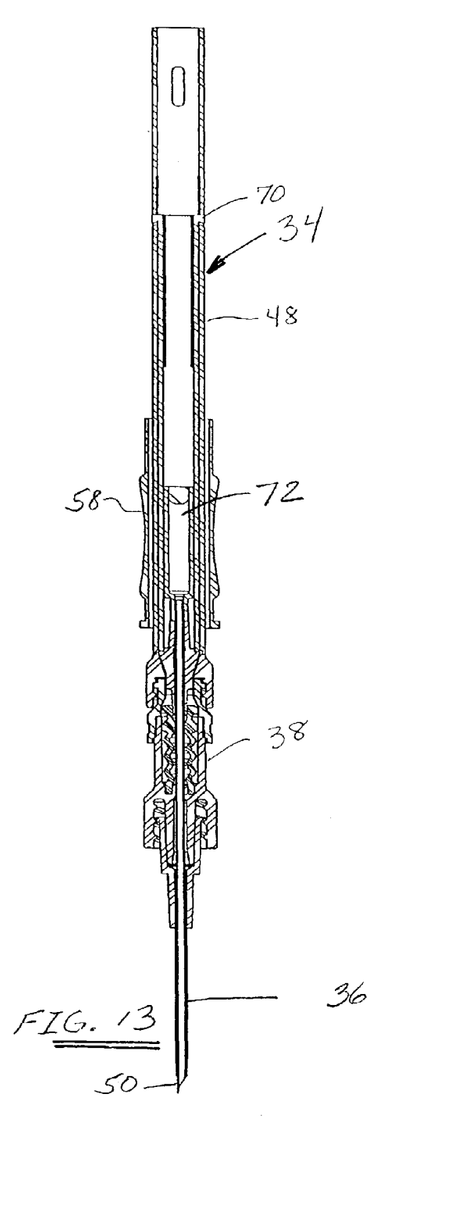
FIG. 13 is a cross-sectional view of FIG. 12.
Figure 14:
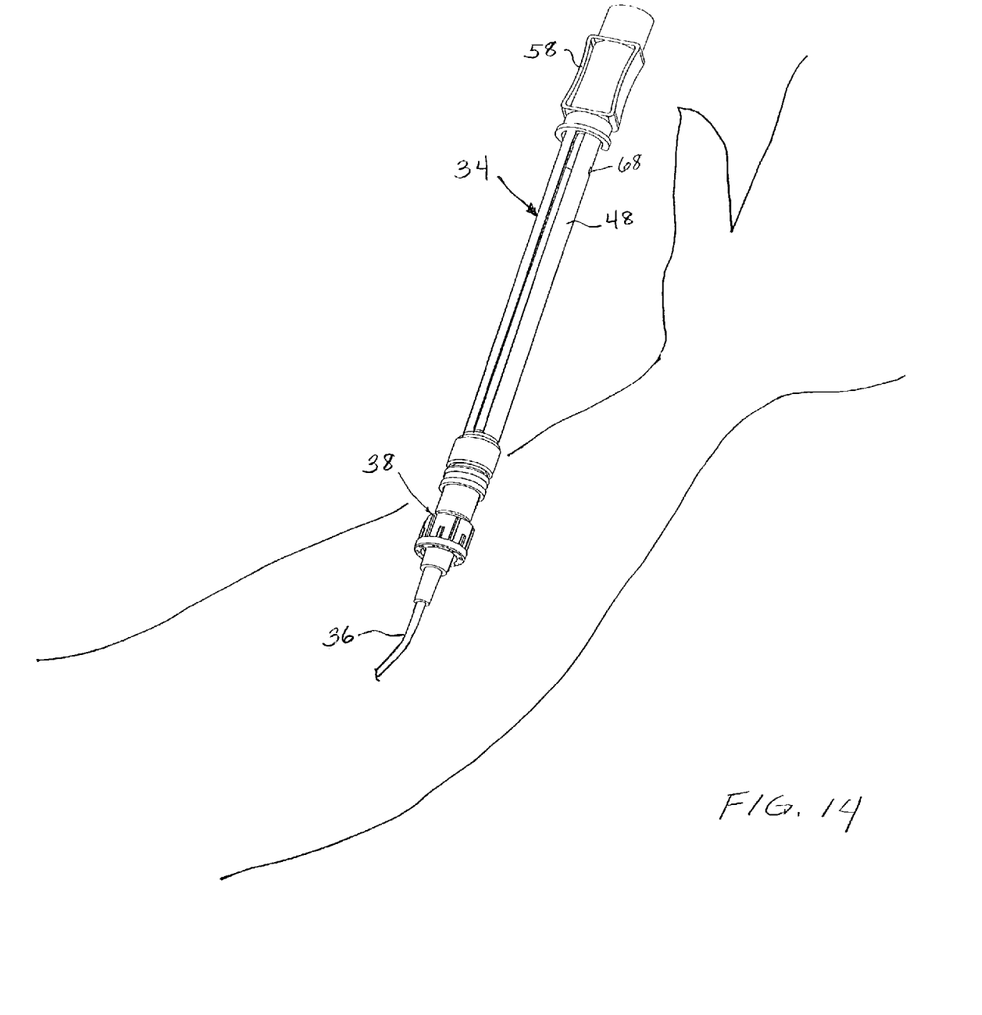
FIG. 14 is a schematic view showing the operation of the control handle of the needle tube after the venipuncture procedure has been completed.

The above is accomplished with a single distal motion. However, once the locking tabs 70 have become located within the slots 68, the sharp needle 50 will be free to extend distally beyond the blunt cannula 62. Then, continuing without interrupting the same distal motion, the control handle 58 is further slid toward the distal end of the insertion mechanism until it reaches the end of its travel, as exemplified in FIGS. 12 and 13. The length of the catheter 36 is selected such that, at this stage of operation, the distal tip of the sharp needle 50 will protrude from the catheter 36 a distance sufficient to permit the successful completion of a venipuncture procedure as shown in FIG. 14. Once the catheter has been positioned properly in the patient's vein, as is indicated by the flow of the patient's blood into the attached flashback chamber 72 for example, the sharp needle 50 is then retracted into the protective needle tube 48 by moving the control handle 58 in the proximal direction and locking the control handle in the retracted position, as is also shown in FIG. 14.

Figure 15:
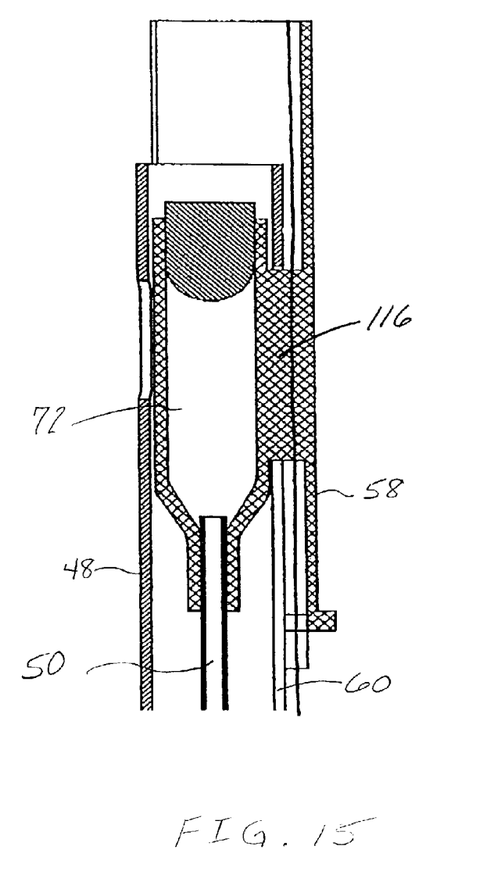
FIG. 15 is a side cross-sectional view of the proximal end of the needle tube showing the connection of the control handle with a flashback chamber attached to the sharp needle.
Figure 16:
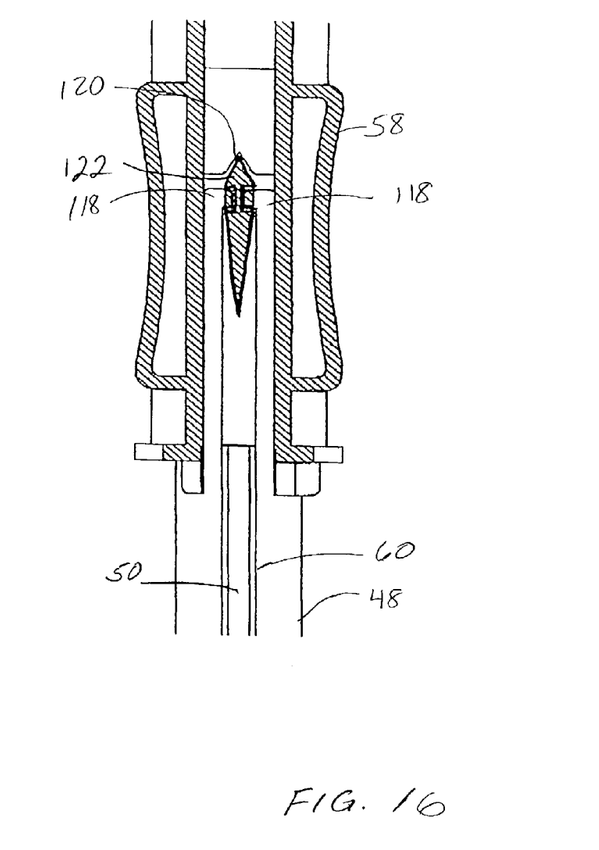
FIG. 16 is a rotated view of part of FIG. 15 showing a control handle lock that will function to retain the sharp needle within the needle tube permanently.

An exemplary locking mechanism is shown in FIGS. 15 and 16. In particular, FIG. 15 shows the connection between the control handle 58 and the flashback chamber 72. A connection arm 116 provides a rigid connection between the control handle 58 and the flashback chamber 72, which in turn is connected to the sharp needle 50. Therefore, movement of the control handle will cause movement of the sharp needle. Conversely, securing the control handle in a fixed position will prevent movement of the sharp needle. A control handle locking device is provided to retain the sharp needle 50 within the needle tube 48 once it has been retracted. As is seen in FIG. 1, a pair of locking arms 118 face each other, yet are spaced apart. A locking notch 120 provides for movement in the proximal direction from the locking arms. Referring now to FIG. 16, a partial cross-section composite of the locking approach in this embodiment is shown. Particularly apparent is that the locking arm 116 includes a triangularly-shaped anchor segment 122. As the control handle is moved in the proximal direction, the point of the anchor segment moves between the locking arms 118 separating them, and then moves into the locking notch. As the bottom of the triangular anchor clears the locking arms 118, they spring back to their closed configuration, as seen in FIG. 1, preventing distal movement of the control handle and sharp needle. The sharp needle is then permanently locked within the needle tube 48 thereby protecting clinicians or others who may handle the insertion mechanism in the future. The insertion mechanism 34 can then be separated from the safety catheter device 32 as shown in FIG. 17, and discarded.

Figure 17:
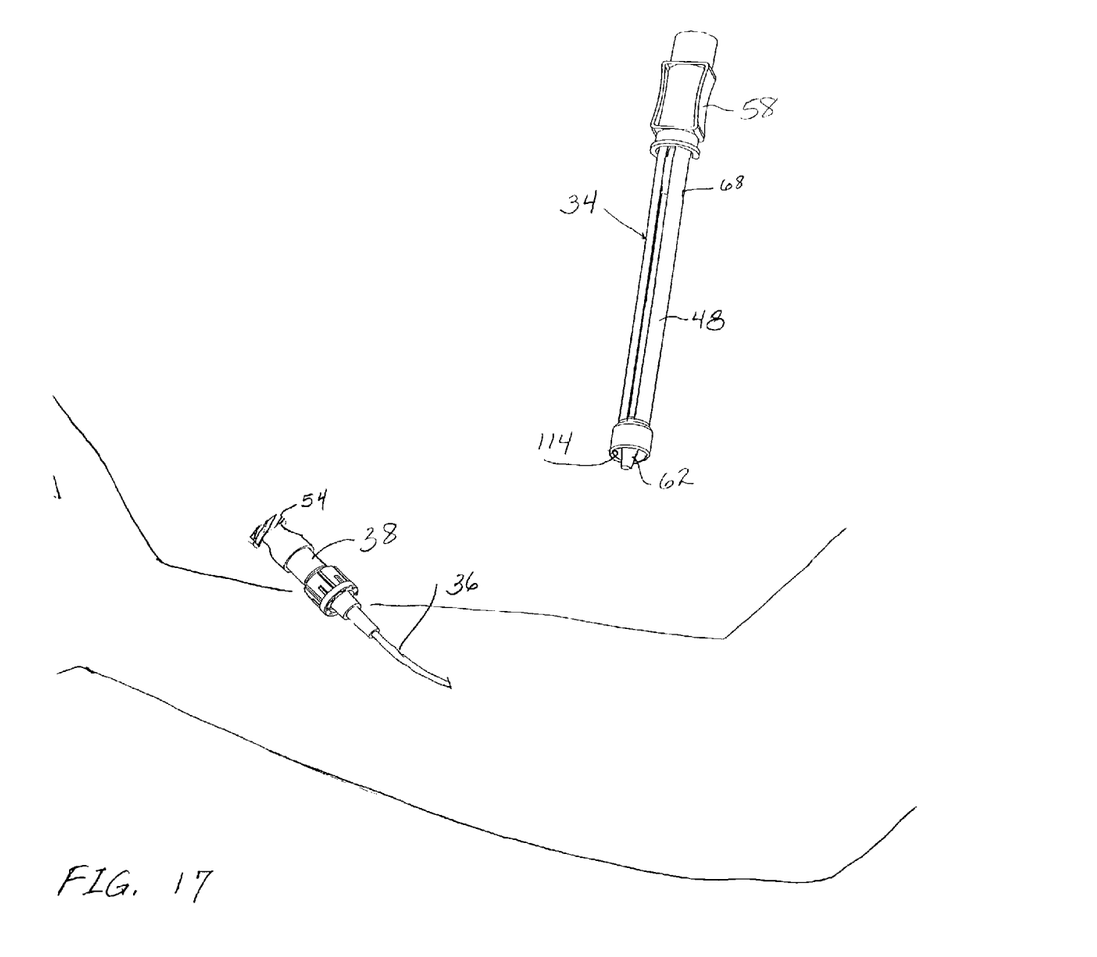
FIG. 17 is a schematic view showing the disconnection of the insertion mechanism from the connector/catheter device after the biological site has been accessed.

When the control handle 58 has been retracted to the position shown in FIG. 17, the blunt cannula 62 will remain extended. As the needle tube 48 is unthreaded from the connector, movement of the blunt cannula in the proximal direction will permit the spring 86 of the connector to force the piston head 88 once again into the smaller size female Luer port 76 causing the marquise-shaped bore 92 to close, preventing blood from flowing from the catheter out of the connector 38. A site is now available through the connector 38 to the patient's circulatory system.

Figure 18:
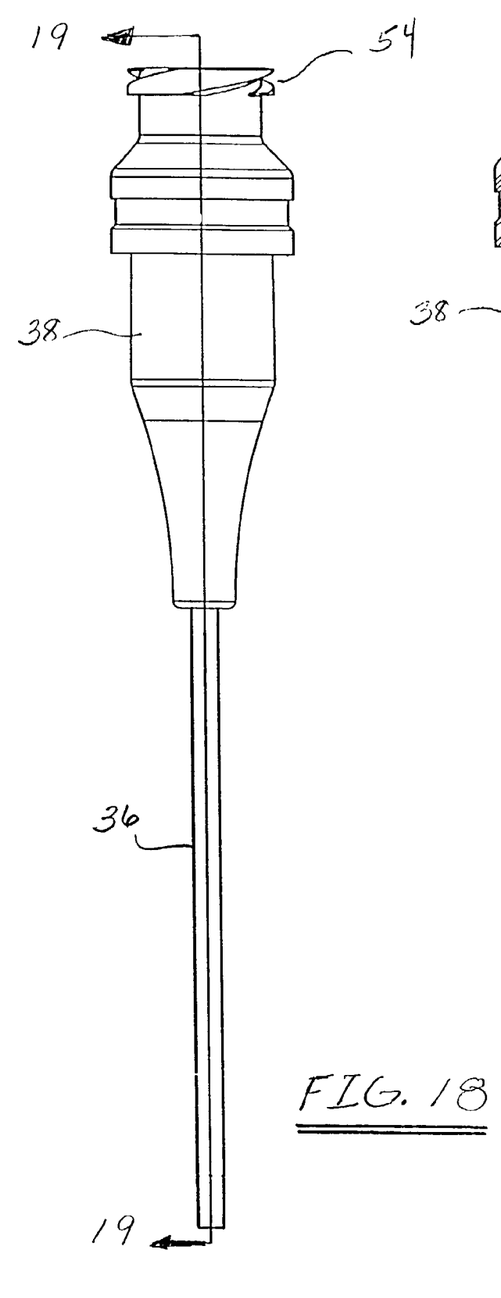
FIGS. 18 and 19 are respectively a full, side, elevation view and a cross-sectional view of an alternate safety catheter connector/catheter device showing the valved connector and the flexible catheter permanently mounted together.
Figure 19:
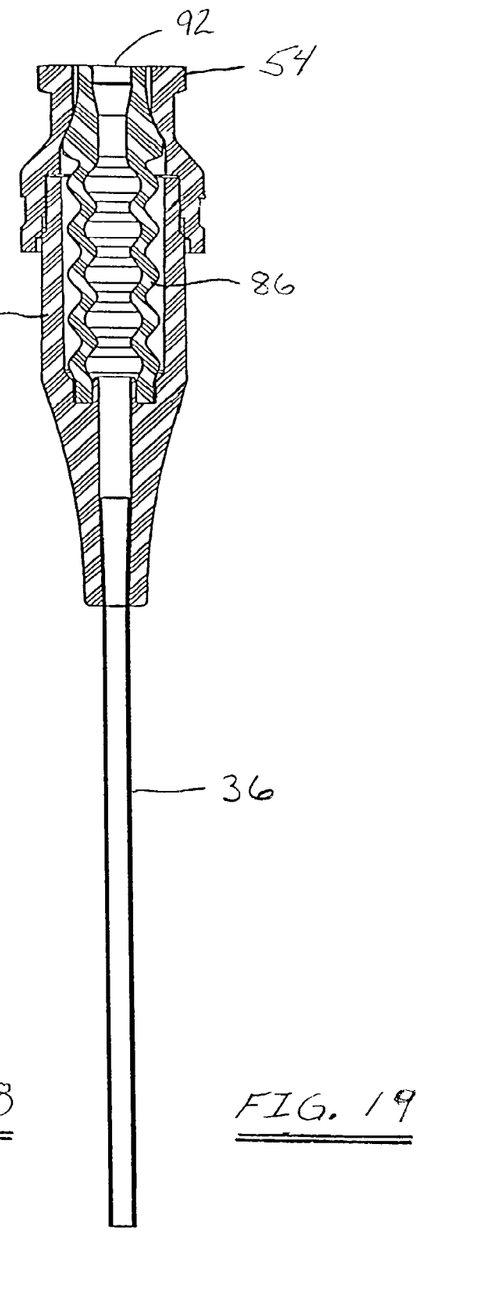
Figure 20:
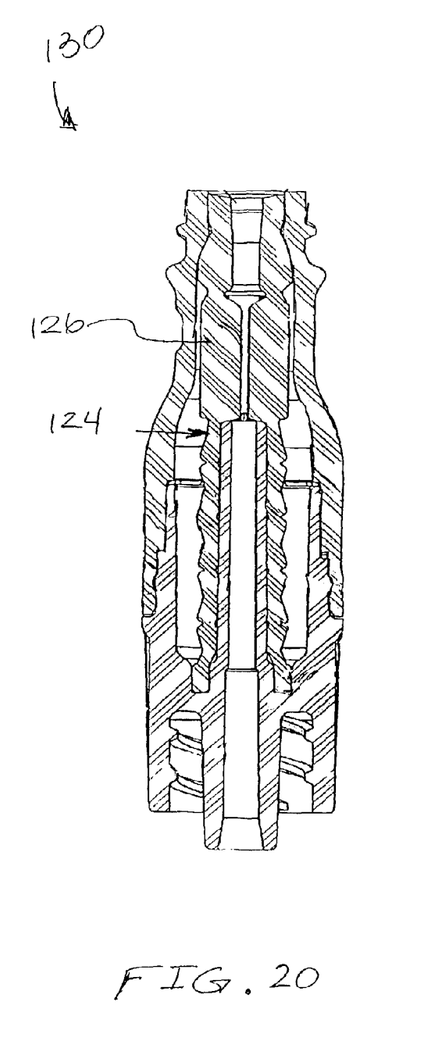
FIGS. 20 and 21 are cross-sectional views of a positive bolus valved connector usable with the safety catheter system in accordance with an alternate embodiment.
Figure 21:
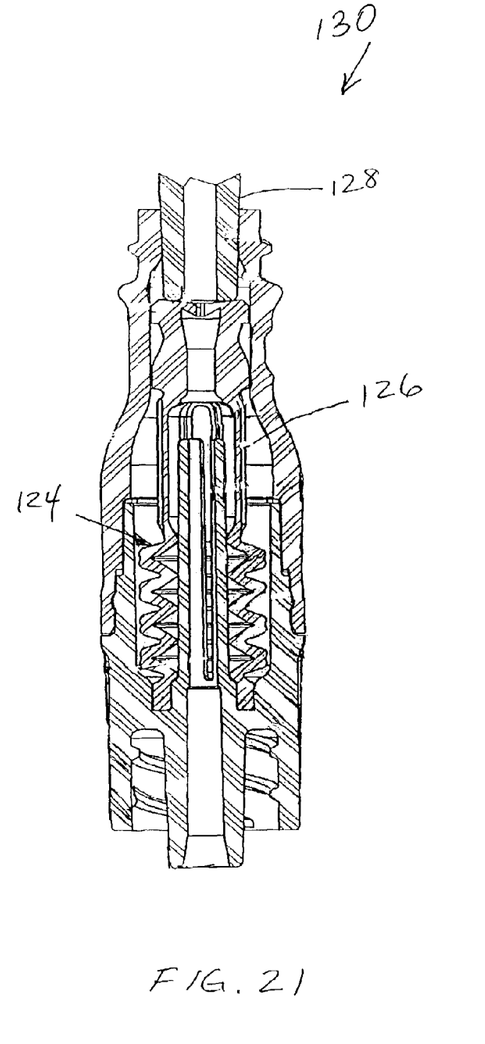

Various details have not been discussed above so that clarity of the description would be preserved. However, it will be appreciated by those skilled in the art that various changes may be made that do not depart from the scope of the invention. For example, a one way filter or valve may be included with the flashback chamber 72 so that blood remains in the chamber when the insertion mechanism is removed from the connector 38, as shown in FIG. 17. Referring to FIGS. 18 and 19, the catheter 36 is shown permanently attached to the distal port 44 of the connector 38. This reduces the number of components by combining the catheter hub with the connector housing 38. Another variation if shown in FIGS. 20 and 21 in which the piston element 124 includes a normally expanded section 126 so that a neutral or positive bolus results when a male Lucr tip 128 is withdrawn from the female port 56. Although a male Luer is shown in FIG. 21, the positive bolus connector 130 may accept the blunt cannula shown and described above. Further details of the positive bolus connector of FIGS. 20 and 21 may be found in application Ser. No. 09/998,383, presently pending, and incorporated herein by reference.

Further, a needle tube 48 was shown and described as providing a sharp needle protection device located so as to provide a physical barrier at the sharp tip of the needle to protect users of the insertion mechanism from being punctured by the sharp tip. However, other embodiments may be possible including a self blunting needle in which a dull rod extends from the lumen of the sharp needle past the sharp tip to protect users from the sharp tip.

Although specific embodiments of the invention have been described and illustrated, it will be apparent to those skilled in the art that modifications and improvements may be made to the devices disclosed herein without departing from the scope of the invention. Accordingly, it is not intended that the invention be limited, except as by the appended claims.

What is claimed is:

1. An insertion mechanism comprising:
   a needle tube having a distal end and a proximal end and comprising a locking slot, the needle tube configured to removably couple to a needleless connector having a flexible catheter;
   a cannula control tube slidably disposed within the needle tube, the cannula control tube comprising a distal position and a fixedly attached blunt cannula at a distal end and a locking tab configured to move outward and engage the locking slot when the cannula control tube is in the distal position; and
   a sharp needle movably disposed within the cannula control tube, such that the needle is axially slidable relative to the cannula control tube, and comprising a distal tip and configured to urge the cannula control tube toward the distal position as the needle is moved toward the distal end of the needle tube;
   wherein the locking tab of the cannula control tube and the needle are configured to allow the distal tip of the needle to extend beyond the distal end of the needle tube and into the flexible catheter of a coupled needleless connector only after the locking tab is engaged in the locking slot of the needle tube.

2. The insertion mechanism of claim 1, wherein:
   the needle further comprises a proximal position and an anchor segment;
   the needle tube further comprises a locking arm configured to engage the anchor segment when the needle is in the proximal position; and
   the needle tube and the needle are configured such that the distal tip of the needle is disposed with the needle tube and the needle cannot be moved in the distal direction when the locking arm is engaged with the anchor segment.

3. The insertion mechanism of claim 1, wherein the needle tube comprises a flashback chamber fluidically connected to the distal tip.

4. The insertion mechanism of claim 3, wherein:
   the locking tab comprises an internal gap having a first value when the locking tab is not engaged with the locking slot and a second value when the locking tab is engaged in the locking slot, the second value being larger than the first value;
   the flashback chamber comprises an outside width having a value that is between the first and second values of the gap of the locking tab;
   the needle and the cannula control tube are configured such that the distal tip of the needle does not extend beyond the blunt cannula when the flashback chamber is disposed on a proximal side of the locking tab; and
   the flashback chamber and the locking tab are configured such that the flashback chamber cannot move past the locking tab toward the distal end of the needle tube when the locking tab is not engaged in the locking slot.

5. The insertion mechanism of claim 3, wherein the needle tube and the flashback chamber are formed of a clear material.

6. The insertion mechanism of claim 3, wherein:
   the needle tube further comprises an access slot with proximal and distal ends; and
   the needle further comprises a handle that extends through the access slot.

7. An insertion mechanism comprising:
   a needle tube having a distal end and a proximal end and comprising a locking slot, the needle tube configured to removably couple to a needleless connector having a flexible catheter;
   a cannula control tube slidably disposed within the needle tube, the cannula control tube comprising a distal position and a fixedly attached blunt cannula at a distal end and a locking tab configured to move outward and engage the locking slot when the cannula control tube is in the distal position; and
   a sharp needle movably disposed within the cannula control tube and comprising a distal tip and configured to urge the cannula control tube toward the distal position as the needle is moved toward the distal end of the needle tube, the needle further comprises a proximal position and an anchor segment;
   wherein the locking tab of the cannula control tube and the needle are configured to allow the distal tip of the needle to extend beyond the flexible catheter of a coupled needleless connector only after the locking tab is engaged in the locking slot of the needle tube;
   wherein the needle tube further comprises a locking arm configured to engage the anchor segment when the needle is in the proximal position and the needle tube and the needle are configured such that the distal tip of the needle is disposed with the needle tube and the needle cannot be moved in the distal direction when the locking arm is engaged with the anchor segment;
   wherein the needle tube, cannula control tube, and needle are configured such that:
   the insertion mechanism comprises an initial configuration wherein the distal tip of the needle is disposed within the blunt cannula and a handle is disposed between the proximal and distal ends of an access slot, wherein coupling of the insertion mechanism to the needleless connector will cause the blunt cannula to open the needleless connector;
   moving the handle toward the distal end of the access slot moves the cannula control tube in the distal direction until the locking tab engages the locking slot of the needle tube;

moving the handle further to the distal end of the access slot extends the needle tip beyond the blunt cannula and into the flexible catheter until the distal tip of the needle extends beyond the catheter; and moving the handle from the distal end of the access slot toward the proximal end of the access slot retracts the distal tip of the needle from the catheter and into the blunt cannula until the locking arm of the needle tube engages the anchor segment of the needle, thereby locking the insertion mechanism into a final configuration wherein the distal tip of the needle is locked within the blunt cannula and the insertion mechanism may be decoupled from the needless connector.

8. The insertion mechanism of claim 7, wherein the needle tube comprises a flashback chamber fluidically connected to the distal tip.

9. The insertion mechanism of claim 8, wherein:

the locking tab comprises an internal gap having a first value when the locking tab is not engaged with the locking slot and a second value when the locking tab is engaged in the locking slot, the second value being larger than the first value;

the flashback chamber comprises an outside width having a value that is between the first and second values of the gap of the locking tab;

the needle and the cannula control tube are configured such that the distal tip of the needle does not extend beyond the blunt cannula when the flashback chamber is disposed on a proximal side of the locking tab; and the flashback chamber and the locking tab are configured such that the flashback chamber cannot move past the locking tab toward the distal end of the needle tube when the locking tab is not engaged in the locking slot.

10. The insertion mechanism of claim 8, wherein the needle tube and the flashback chamber are formed of a clear material.

11. The insertion mechanism of claim 8, wherein:

the needle tube further comprises an access slot with proximal and distal ends; and the needle further comprises a handle that extends through the access slot.

\* \* \* \* \*